US008536382B2

(12) United States Patent
Jevtic et al.

(10) Patent No.: US 8,536,382 B2
(45) Date of Patent: Sep. 17, 2013

(54) PROCESSES FOR HYDROGENATING ALKANOIC ACIDS USING CATALYST COMPRISING TUNGSTEN

(75) Inventors: Radmila Jevtic, Pasadena, TX (US); Victor Johnston, Houston, TX (US); Heiko Weiner, Pasadena, TX (US); Zhenhua Zhou, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 200 days.

(21) Appl. No.: 13/267,149

(22) Filed: Oct. 6, 2011

(65) Prior Publication Data
US 2013/0090500 A1    Apr. 11, 2013

(51) Int. Cl.
    *C07C 29/149* (2006.01)
(52) U.S. Cl.
    USPC ......................................................... 568/885
(58) Field of Classification Search
    USPC ......................................................... 568/885
    See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,478,112 A | 11/1969 | Karl et al. |
| 3,702,886 A | 11/1972 | Argauer et al. |
| 3,729,429 A | 4/1973 | Robson |
| 4,065,512 A | 12/1977 | Cares |
| 4,228,307 A | 10/1980 | Zimmerschied |
| 4,270,015 A | 5/1981 | Knifton et al. |
| 4,275,228 A | 6/1981 | Gruffaz et al. |
| 4,317,918 A | 3/1982 | Takano et al. |
| 4,328,373 A | 5/1982 | Strojny |
| 4,337,351 A | 6/1982 | Larkins |
| 4,374,265 A | 2/1983 | Larkins, Jr. |
| 4,395,576 A | 7/1983 | Kwantes et al. |
| 4,398,039 A | 8/1983 | Pesa et al. |
| 4,399,305 A | 8/1983 | Schreck et al. |
| 4,421,939 A | 12/1983 | Kiff et al. |
| 4,443,639 A | 4/1984 | Pesa et al. |
| 4,465,854 A | 8/1984 | Pond et al. |
| 4,471,136 A | 9/1984 | Larkins et al. |
| 4,480,115 A | 10/1984 | McGinnis |
| 4,517,391 A | 5/1985 | Schuster et al. |
| 4,521,630 A | 6/1985 | Wattimena et al. |
| 4,550,185 A | 10/1985 | Mabry et al. |
| 4,581,473 A | 4/1986 | Polichnowski et al. |
| 4,613,700 A | 9/1986 | Maki et al. |
| 4,620,050 A | 10/1986 | Cognion et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,826,795 A | 5/1989 | Kitson et al. |
| 4,843,170 A | 6/1989 | Isshiki et al. |
| 4,886,905 A | 12/1989 | Larkins et al. |
| 4,978,778 A | 12/1990 | Isshiki et al. |
| 4,985,572 A | 1/1991 | Kitson et al. |
| 4,990,655 A | 2/1991 | Kitson et al. |
| 5,008,235 A | 4/1991 | Wegman et al. |
| 5,061,671 A | 10/1991 | Kitson et al. |
| 5,137,861 A | 8/1992 | Shih et al. |
| 5,149,680 A | 9/1992 | Kitson et al. |
| 5,155,084 A | 10/1992 | Horn et al. |
| 5,185,308 A | 2/1993 | Bartley et al. |
| 5,241,106 A | 8/1993 | Inoue et al. |
| 5,243,095 A | 9/1993 | Roberts et al. |
| 5,306,845 A | 4/1994 | Yokohama et al. |
| 5,350,504 A | 9/1994 | Dessau |
| 5,426,246 A | 6/1995 | Nagahara et al. |
| 5,475,144 A | 12/1995 | Watson et al. |
| 5,476,827 A | 12/1995 | Ferrero et al. |
| RE35,377 E | 11/1996 | Steinberg et al. |
| 5,585,523 A | 12/1996 | Weiguny et al. |
| 5,691,267 A | 11/1997 | Nicolau et al. |
| 5,719,315 A | 2/1998 | Tustin et al. |
| 5,731,456 A | 3/1998 | Tustin et al. |
| 5,767,307 A | 6/1998 | Ramprasad et al. |
| 5,821,111 A | 10/1998 | Gaddy et al. |
| 5,849,657 A | 12/1998 | Rotgerink et al. |
| 5,861,530 A | 1/1999 | Atkins et al. |
| 5,945,570 A | 8/1999 | Arhancet et al. |
| 5,955,397 A | 9/1999 | Didillon et al. |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Yokoyama, et al."Carboxylic Acids and Derivatives", Fine Chemicals through Heterogenous Catalysis, pp. 370-379.

Subramani, et al., "A Review of Recent Literature to Search for an Efficient Catalytic Process for the Conversion of Syngas to Ethanol," Energy & Fuels, 2008, vol. 22, pp. 814-839.

Spivey, et al., "Heterogeneous catalytic synthesis of ethanol from biomass-dervied syngas," Chemical Society Review, 2007, vol. 36, pp. 1514-1528.

Santori et al.(2000). Hydrogenation of carbonylic compounds on Pt/SiO2 catalysts modified with SnBu4, Studies in Surface Science and Catalysis, 130, 2063-2068.

(Continued)

*Primary Examiner* — Elvis O Price

(57) ABSTRACT

A process hydrogenating alkanoic acids in the presence of a catalyst that comprises supports, one or more metals, tungsten oxide, and at least one alkaline earth metal oxide or metasilicate. The molar ratio of the at least one alkaline earth metal oxide or metasilicate to tungsten oxide, based on the metals, is from 1:3 to 5:1.

22 Claims, No Drawings

(56) References Cited

U.S. PATENT DOCUMENTS

| | | | |
|---|---|---|---|
| 5,973,193 | A | 10/1999 | Crane et al. |
| 6,040,474 | A | 3/2000 | Jobson et al. |
| 6,049,008 | A | 4/2000 | Roberts et al. |
| 6,093,845 | A | 7/2000 | Van Acker et al. |
| 6,114,571 | A | 9/2000 | Abel et al. |
| 6,121,498 | A | 9/2000 | Tustin et al. |
| 6,232,352 | B1 | 5/2001 | Vidalin et al. |
| 6,232,504 | B1 | 5/2001 | Barteau et al. |
| 6,294,703 | B1 | 9/2001 | Hara et al. |
| 6,462,231 | B1 | 10/2002 | Yanagawa et al. |
| 6,472,555 | B2 | 10/2002 | Choudary et al. |
| 6,486,366 | B1 | 11/2002 | Ostgard et al. |
| 6,495,730 | B1 | 12/2002 | Konishi et al. |
| 6,509,180 | B1 | 1/2003 | Verser et al. |
| 6,509,290 | B1 | 1/2003 | Vaughn et al. |
| 6,559,333 | B1 | 5/2003 | Brunelle et al. |
| 6,603,038 | B1 | 8/2003 | Hagemeyer et al. |
| 6,632,330 | B1 | 10/2003 | Colley et al. |
| 6,657,078 | B2 | 12/2003 | Scates et al. |
| 6,685,754 | B2 | 2/2004 | Kindig et al. |
| 6,693,213 | B1 | 2/2004 | Kolena et al. |
| 6,696,596 | B1 | 2/2004 | Herzog et al. |
| 6,727,380 | B2 | 4/2004 | Ellis et al. |
| 6,765,110 | B2 | 7/2004 | Warner et al. |
| 6,768,021 | B2 | 7/2004 | Horan et al. |
| 6,812,372 | B2 | 11/2004 | Janssen et al. |
| 6,852,877 | B1 | 2/2005 | Zeyss et al. |
| 6,903,045 | B2 | 6/2005 | Zoeller et al. |
| 6,906,228 | B2 | 6/2005 | Fischer et al. |
| 6,927,048 | B2 | 8/2005 | Verser et al. |
| 7,074,603 | B2 | 7/2006 | Verser et al. |
| 7,084,312 | B1 | 8/2006 | Huber et al. |
| 7,297,236 | B1 | 11/2007 | Vander Griend et al. |
| 7,351,559 | B2 | 4/2008 | Verser et al. |
| 7,375,049 | B2 | 5/2008 | Hayes et al. |
| 7,425,657 | B1 | 9/2008 | Elliott et al. |
| 7,507,562 | B2 | 3/2009 | Verser et al. |
| 7,538,060 | B2 | 5/2009 | Barnicki et al. |
| 7,572,353 | B1 | 8/2009 | Vander et al. |
| 7,608,744 | B1 | 10/2009 | Johnston et al. |
| 7,863,489 | B2 | 1/2011 | Johnston et al. |
| 7,884,253 | B2 | 2/2011 | Stites et al. |
| 2003/0013908 | A1 | 1/2003 | Horan et al. |
| 2003/0077771 | A1 | 4/2003 | Verser et al. |
| 2003/0104587 | A1 | 6/2003 | Verser et al. |
| 2003/0114719 | A1 | 6/2003 | Fischer et al. |
| 2003/0191020 | A1 | 10/2003 | Bharadwaj et al. |
| 2004/0195084 | A1 | 10/2004 | Hetherington et al. |
| 2006/0019360 | A1 | 1/2006 | Verser et al. |
| 2006/0102520 | A1 | 5/2006 | Lapinski et al. |
| 2006/0127999 | A1 | 6/2006 | Verser et al. |
| 2007/0106246 | A1 | 5/2007 | Modesitt |
| 2007/0270511 | A1 | 11/2007 | Melnichuk et al. |
| 2008/0207953 | A1 | 8/2008 | Houssin et al. |
| 2009/0005588 | A1 | 1/2009 | Hassan et al. |
| 2009/0023192 | A1 | 1/2009 | Verser et al. |
| 2009/0081749 | A1 | 3/2009 | Verser et al. |
| 2009/0166172 | A1 | 7/2009 | Casey et al. |
| 2009/0221725 | A1 | 9/2009 | Chorney et al. |
| 2009/0326080 | A1 | 12/2009 | Chornet et al. |
| 2010/0016454 | A1 | 1/2010 | Gracey et al. |
| 2010/0029995 | A1 | 2/2010 | Johnston et al. |
| 2010/0029996 | A1 | 2/2010 | Danjo et al. |
| 2010/0113843 | A1 | 5/2010 | Lee et al. |
| 2010/0121114 | A1 | 5/2010 | Johnston et al. |
| 2010/0168493 | A1 | 7/2010 | Le Peltier et al. |
| 2010/0196789 | A1 | 8/2010 | Fisher et al. |
| 2010/0249479 | A1 | 9/2010 | Berg-Slot et al. |

FOREIGN PATENT DOCUMENTS

| | | |
|---|---|---|
| CN | 102229520 | 11/2011 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0330853 | 9/1989 |
| EP | 0400904 | 5/1990 |
| EP | 0372847 | 6/1990 |
| EP | 0408528 | 7/1990 |
| EP | 0990638 | 4/2000 |
| EP | 1262234 | 12/2002 |
| EP | 1277826 | 1/2003 |
| EP | 2060553 | 5/2009 |
| EP | 2060555 | 5/2009 |
| EP | 2186787 | 5/2010 |
| GB | 1168785 | 10/1969 |
| GB | 1559540 | 1/1980 |
| GB | 2136704 | 9/1984 |
| JP | 03-220143 | 9/1991 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 83/03409 | 10/1983 |
| WO | WO 03/040037 | 5/2003 |
| WO | WO 2005/102513 | 11/2005 |
| WO | WO 2009/009322 | 1/2009 |
| WO | WO 2009/009323 | 1/2009 |
| WO | WO 2009/063176 | 5/2009 |
| WO | WO 2009/086839 | 7/2009 |
| WO | WO 2009/105860 | 9/2009 |
| WO | WO 2010/014145 | 2/2010 |
| WO | WO 2010/014151 | 2/2010 |
| WO | WO 2010/014153 | 2/2010 |
| WO | WO 2010/055285 | 5/2010 |
| WO | WO 2011/053365 | 5/2011 |

OTHER PUBLICATIONS

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., The formation of ketones and aldehydes from carboxylic acids, structure-activity relationship for two competitive reactions, Journal of Molecular Catalysis A: Chemical 103 Jun. 14, 1995, 175-180.

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

Proc. Roy Soc. A314, pp. 473-498 (1970).

Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.

Liberkova, and Tourounde, "Performance of Pt/SnO2 catalyst in the gas phase hydrogenation of crotonaldehyde," J. Mol. Catal. A: Chemical (2002), 180, p. 221-230.

Rodrigues and Bueno, "Co/SiO2 catalysts for selective hydrogenation of crotonaldehyde: III. Promoting effect of zinc," Applied Catalysis A: General (2004), 257, p. 210-211.

Ammari, et al. "An emergent catalytic material: Pt/ZnO catalyst for selective hydrogenation of crotonaldehyde," J. Catal. (2004), 221, p. 32-42.

Ammari, et al. "Selective hydrogenation of crotonaldehyde on Pt/ZnCl2/SiO2 catalysts," J. Catal. (2005), 235, p. 1-9.

Consonni, et al. "High Performances of Pt/ZnO Catalysts in Selective Hydrogenation of Crotonaldehyde," J. Catal. (1999), 188, p. 165-175.

Nitta, et al. "Selective hydrogenation of $\alpha\beta$-unsaturated aldehydes on cobalt—silica catalysts obtained from cobalt chrysotile," Applied Catal. (1989), 56, p. 9-22.

Brunauer Emmett and Teller, J. Am. Chem. Soc. 60, 309 (1938).

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

International Search Report and Written Opinion for PCT/US2010/022947 mailed Jun. 7, 2010.

International Search Report and Written Opinion for PCT/US2010/022949 mailed Jun. 7, 2010.

Invitation to Pay Fees and Partial Search Report for PCT/US2010/022950 mailed Jun. 15, 2010.

International Search Report and Written Opinion for PCT/US2010/022950 mailed Sep. 7, 2011.

International Search Report and Written Opinion for PCT/US2010/022953 mailed Jun. 7 2010.

International Search Report and Written Opinion for PCT/US2010/054134 mailed Feb. 28, 2011.

International Search Report and Written Opinion mailed Jan. 31, 2013 in corresponding International Application No. PCT/US2012/061794.

PROCESSES FOR HYDROGENATING ALKANOIC ACIDS USING CATALYST COMPRISING TUNGSTEN

FIELD OF THE INVENTION

The present invention relates generally to processes for hydrogenating alkanoic acids, in particular acetic acid, to form alcohols and to novel catalysts for use in such processes.

BACKGROUND OF THE INVENTION

There is a long felt need for an economically viable process to convert acetic acid to ethanol which may be used in its own right or subsequently converted to ethylene which is an important commodity feedstock as it can be converted to vinyl acetate and/or ethyl acetate or any of a wide variety of other chemical products. For example, ethylene can also be converted to numerous polymer and monomer products. Fluctuating natural gas and crude oil prices contribute to fluctuations in the cost of conventionally produced, petroleum or natural gas-sourced ethylene, making the need for alternative sources of ethylene all the greater when oil prices rise.

Catalytic processes for reducing alkanoic acids and other carbonyl group containing compounds have been widely studied, and a variety of combinations of catalysts, supports and operating conditions have been mentioned in the literature. The reduction of various carboxylic acids over metal oxides is reviewed by T. Yokoyama et al. in "Fine chemicals through heterogeneous catalysis. Carboxylic acids and derivatives." Chapter 8.3.1, summarizes some of the developmental efforts for hydrogenation catalysts for various carboxylic acids. (Yokoyama, T.; Setoyama, T. "Carboxylic acids and derivatives." in: "Fine chemicals through heterogeneous catalysis." 2001, 370-379.)

A series of studies by M. A. Vannice et al. concern the conversion of acetic acid over a variety of heterogeneous catalysts (Rachmady W.; Vannice, M. A.; *J. Catal.* (2002) Vol. 207, pg. 317-330.) The vapor-phase reduction of acetic acid by $H_2$ over both supported and unsupported iron was reported in a separate study. (Rachmady, W.; Vannice, M. A. *J. Catal.* (2002) Vol. 208, pg. 158-169.) Further information on catalyst surface species and organic intermediates is set forth in Rachmady, W.; Vannice, M. A., *J. Catal.* (2002) Vol. 208, pg. 170-179). Vapor-phase acetic acid hydrogenation was studied further over a family of supported Pt—Fe catalysts in Rachmady, W.; Vannice, M. A. *J. Catal.* (2002) Vol. 209, pg. 87-98) and Rachmady, W.; Vannice, M. A. *J. Catal.* (2000) Vol. 192, pg. 322-334).

Various related publications concerning the selective hydrogenation of unsaturated aldehydes may be found in (Djerboua, F.; Benachour, D.; Touroude, R. Applied Catalysis A: General 2005, 282, 123-133.; Liberkova, K.; Tourounde, R. *J. Mol. Catal.* 2002, 180, 221-230.; Rodrigues, E. L.; Bueno, J. M. C. Applied Catalysis A: General 2004, 257, 210-211.; Ammari, F.; Lamotte, J.; Touroude, R. *J. Catal.* 2004, 221, 32-42; Ammari, F.; Milone, C.; Touroude, R. J. Catal. 2005, 235, 1-9.; Consonni, M.; Jokic, D.; Murzin, D. Y.; Touroude, R. *J. Catal.* 1999, 188, 165-175.; Nitta, Y.; Ueno, K.; Imanaka, T.; Applied Catal. 1989, 56, 9-22.)

Studies reporting activity and selectivity over cobalt, platinum and tin-containing catalysts in the selective hydrogenation of crotonaldehyde to the unsaturated alcohol are found in R. Touroude et al. (Djerboua, F.; Benachour, D.; Touroude, R. Applied Catalysis A: General 2005, 282, 123-133 as well as Liberkova, K.; Touronde, R.; *J. Mol. Catal.* 2002, 180, 221-230) as well as K. Lazar et al. (Lazar, K.; Rhodes, W. D.; Borbath, I.; Hegedues, M.; Margitfalvi, 1. L. *Hyperfine Interactions* 2002, 1391140, 87-96.)

M. Santiago et al. (Santiago, M. A. N.; Sanchez-Castillo, M. A.; Cortright, R. D.; Dumesic, 1. A. *J. Catal.* 2000, 193, 16-28.) discuss microcalorimetric, infrared spectroscopic, and reaction kinetics measurements combined with quantum-chemical calculations.

Catalytic activity in for the acetic acid hydrogenation has also been reported for heterogeneous systems with rhenium and ruthenium. (Ryashentseva, M. A.; Minachev, K. M.; Buiychev, B. M.; Ishchenko, V. M. *Bull. Acad Sci. USSR* 1988, 2436-2439).

U.S. Pat. No. 5,149,680 to Kitson et al. describes a process for the catalytic hydrogenation of carboxylic acids and their anhydrides to alcohols and/or esters utilizing platinum group metal alloy catalysts admixed with a component comprising at least one of the metals rhenium, tungsten or molybdenum. U.S. Pat. No. 4,777,303 to Kitson et al. describes a process for the productions of alcohols by the hydrogenation of carboxylic acids. U.S. Pat. No. 4,804,791 to Kitson et al. describes another process for the production of alcohols by the hydrogenation of carboxylic acids. See also U.S. Pat. Nos. 5,061, 671 4,990,655, 4,985,572, and 4,826,795.

Malinowski et al. (*Bull. Soc. Chim. Belg.* (1985), 94(2), 93-5), discuss reaction catalysis of acetic acid on low-valent titanium heterogenized on support materials such as silica ($SiO_2$) or titania ($TiO_2$).

Bimetallic ruthenium-tin/silica catalysts have been prepared by reaction of tetrabutyl tin with ruthenium dioxide supported on silica. (Loessard et al., *Studies in Surface Science and Catalysis* (1989), Volume Date 1988, 48 (*Struct. React. Surf.*), 591-600.)

The catalytic reduction of acetic acid has also been studied in, for instance, Hindermann et al., (Hindermann et al., *J. Chem. Res., Synopses* (1980), (11), 373), disclosing catalytic reduction of acetic acid on iron and on alkali-promoted iron.

Improvements to hydrogenation catalysts are needed.

SUMMARY OF THE INVENTION

In a first embodiment, the present invention is directed to process for producing alcohol comprising passing a gaseous stream comprising hydrogen and an alkanoic acid in the vapor phase over a hydrogenation catalyst to yield an alcohol. The hydrogenation catalyst comprising a support and one or more metals, wherein the hydrogenation catalyst further comprises: (a) tungsten oxide, and (b) at least one alkaline earth metal oxide, at least one alkaline earth metal metasilicate, or mixtures thereof In one embodiment, the molar ratio, based on the metals, of component (b) to component (a) is from 1:3 to 5:1.

In a second embodiment, the present invention is directed to process for producing alcohol comprising passing a gaseous stream comprising hydrogen and an alkanoic acid in the vapor phase over a hydrogenation catalyst to yield an alcohol, wherein the hydrogenation catalyst comprises (a) support, (b) tin, (c) one or more metals selected from the group consisting of rhodium, platinum, palladium, cobalt, copper, iron, nickel, zinc, chromium, rhenium, molybdenum, and ruthenium, (d) tungsten oxide, (e) at least one alkaline earth metal oxide and alkaline earth metal metasilicate. In one embodiment, the molar ratio, based on the metals, of component (e) to component (d) is from 1:3 to 5:1.

In a third embodiment, the present invention is directed to a hydrogenation catalyst for producing alcohol, the hydrogenation catalyst comprises a support and one or more metals, wherein the hydrogenation catalyst further comprises: (a) tungsten oxide, (b) at least one alkaline earth metal oxide, at least one alkaline earth metal metasilicate, or mixtures thereof, and wherein the molar ratio, based on the metals, of component (b) to component (a) is from 1:3 to 5:1.

In a fourth embodiment, the present invention is directed to a hydrogenation catalyst for producing alcohol, the hydrogenation catalyst comprises a (a) support, (b) tin, (c) one or more metals selected from the group consisting of rhodium, platinum, palladium, cobalt, copper, iron, nickel, zinc, chromium, rhenium, molybdenum, and ruthenium, (d) tungsten oxide, (e) at least one alkaline earth metal oxide and alkaline earth metal metasilicate, and wherein the molar ratio, based on the metals, of component (e) to component (d) is from 1:3 to 5:1.

DETAILED DESCRIPTION OF THE INVENTION

The present invention relates to processes for producing ethanol by hydrogenating alkanoic acid, for example acetic acid, in the presence of a catalyst. The catalyst employed in the process comprises one or more metals on a support, and the support further comprises tungsten oxide ($WO_3$), and at least one alkaline earth metal oxide or metasilicate. The present invention has found that when the molar ratio, based on the metal, of the at least one alkaline earth metal to tungsten is preferably from 1:3 to 5:1, e.g., from 1:2 to 3:1 and preferably about 1:1 to 2:1. In preferable embodiments the alkaline earth metal metasilicate is calcium metasilicate (Ca-$SiO_3$), and the molar ratio, based on the metal, calcium to tungsten is from 1:3 to 5:1, e.g., from 1:2 to 3:1, and preferably about 1:1. In one embodiment, the molar ratios may provide increased catalyst activity leading to higher acid conversions and higher overall ethanol yields.

The present invention also relates to the catalysts used in a hydrogenation process and processes for making the catalysts. One particular preferred reaction is to make ethanol from acetic acid. The hydrogenation reaction may be represented as follows:

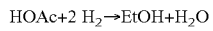

It has surprisingly and unexpectedly been discovered that the catalysts of the present invention provide high selectivity to ethanol when employed in the hydrogenation of alkanoic acids. Embodiments of the present invention beneficially may be used in industrial applications to produce ethanol on an economically feasible scale.

The catalyst of the invention comprises one or more metals. The one or more metals may be selected from the group consisting of tin, rhodium, platinum, palladium, cobalt, copper, iron, nickel, zinc, chromium, rhenium, molybdenum, and ruthenium. Preferably, the one or more metals comprise at least tin and other one metal, selected from the group consisting of rhodium, platinum, palladium, cobalt, copper, iron, nickel, zinc, chromium, rhenium, molybdenum, and ruthenium. The total weight of all supported metals present in the catalyst preferably is from 0.1 to 25 wt. %, e.g., from 0.1 to 15 wt. %, or from 0.1 wt. % to 10 wt. %. The individual amounts of the metals may vary. For example, the amount of tin may be present in an amount from 0.1 to 20 wt. %, e.g., from 0.1 to 10 wt. %, or from 0.1 to 5 wt. %.

For purposes of the present specification, unless otherwise indicated, weight percent is based on the total weight the catalyst including metal and support. The metal(s) in the catalyst may be present in the form of one or more metal oxides. For purposes of determining the weight percent of the metal(s) in the catalyst, the weight of any oxygen that is bound to the metal is ignored.

Depending primarily on how the catalyst is manufactured, the metals of the catalysts of the present invention may be dispersed throughout the support, coated on the outer surface of the support (egg shell) or decorated on the surface of the support.

The catalysts of the present invention may be any suitable support. In one embodiment, the support may be a silicaceous support selected from the group consisting of silica, silica/alumina, calcium metasilicate, pyrogenic silica, high purity silica, and mixtures thereof. In preferred embodiments, the support is present in an amount from 25 wt. % to 99 wt. %, e.g., from 30 wt. % to 97 wt. % or from 35 wt. % to 95 wt. %.

The surface area of the silicaceous support material, e.g., silica, preferably is at least about 50 $m^2/g$, e.g., at least about 100 $m^2/g$, at least about 150 $m^2/g$, at least about 200 $m^2/g$ or most preferably at least about 250 $m^2/g$. In terms of ranges, the silicaceous support material preferably has a surface area of from 50 to 600 $m^2/g$, e.g., from 100 to 500 $m^2/g$ or from 100 to 300 $m^2/g$. High surface area silica, as used throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The silicaceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 $cm^3/g$, e.g., from 0.7 to 1.5 $cm^3/g$ or from about 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density of from 0.1 to 1.0 $g/cm^3$, e.g., from 0.2 to 0.9 $g/cm^3$ or from 0.5 to 0.8 $g/cm^3$. In terms of size, the silica support material preferably has an average particle size, e.g., meaning the diameter for spherical particles or equivalent spherical diameter for non-spherical particles, of from 0.01 to 1.0 cm, e.g., from 0.1 to 0.5 cm or from 0.2 to 0.4 cm. Since the one or more metal(s) that are disposed on or within the modified support are generally very small in size, they should not substantially impact the size of the overall catalyst particles. Thus, the above particle sizes generally apply to both the size of the modified supports as well as to the final catalyst particles.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$.

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

On the support, there may be tungsten oxide and at least one alkaline earth metal oxide or metasilicate, referred to as support modifiers, in the molar ratio. In preferred embodiments, the total weight of the support modifiers are present in an amount from 0.1 wt. % to 50 wt. %, e.g., from 0.2 wt. % to 25 wt. %, from 0.5 wt. % to 20 wt. %, or from 1 wt. % to 18 wt. %, based on the total weight of the catalyst. In one embodiment, the tungsten oxide modifiers may be present in an amount from 1 wt. % to 25 wt. %, e.g., from 3 wt. % to 20 wt. %, or from 5 wt. % to 15 wt. %, based on the total weight of the catalyst. In preferred embodiments, the at least one alkaline earth metal oxide or metasilicate may be present in an amount from 0.2 wt. % to 25 wt. %, e.g., from 0.5 wt. % to 12 wt. %, or from 1 wt. % to 8 wt. %, based on the total weight of the catalyst.

Support modifiers may adjust the acidity of the support. For example, the acid sites, e.g. Bronsted acid sites, on the support material may be adjusted by the support modifier to favor selectivity to ethanol during the hydrogenation of acetic acid. The acidity of the support material may be adjusted by reducing the number or reducing the availability of Bronsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. It has now been discovered that in addition to the metal precursors and preparation conditions employed, metal-support interactions may have a strong impact on selectivity to ethanol. In particular, the use of modified supports that adjust the acidity of the support to make the support less acidic or more basic surprisingly and unexpectedly has now been demonstrated to favor formation of ethanol over other hydrogenation products.

As will be appreciated by those of ordinary skill in the art, supports and support modifiers are selected such that the catalyst system is suitably active, selective and robust under the process conditions employed for the formation of ethanol.

Such basic modifiers, for example, may be selected from the group consisting of alkaline earth metal oxides, alkaline earth metal metasilicates, and mixtures thereof. Preferably, the alkaline earth metal is selected from the group consisting of magnesium, calcium, and mixtures thereof. Preferably, the support modifier is a calcium metasilicate ($CaSiO_3$). If the support modifier comprises calcium metasilicate, it is preferred that at least a portion of the calcium metasilicate is in crystalline form.

Accordingly, without being bound by theory, modification and stabilization of oxidic support materials for the catalysts of the present invention by incorporation of non-volatile support modifiers having the effect of: counteracting acid sites present upon the support surface or the effect of thermally stabilizing the surface makes it possible to achieve desirable improvements in selectivity to ethanol, prolonged catalyst life, or both. In general, support modifiers based on oxides in their most stable valence state will have low vapor pressures and thus have low volatility or are rather non-volatile. Accordingly, it is preferred that the support modifiers are provided in amounts sufficient to: (i) counteract acidic sites present on the surface of the support material; (ii) impart resistance to shape change under hydrogenation temperatures; or (iii) both. Without being bound by theory, imparting resistance to shape change refers to imparting resistance, for example, to sintering, grain growth, grain boundary migration, migration of defects and dislocations, plastic deformation and/or other temperature induced changes in microstructure.

Catalysts of the present invention are particulate catalysts in the sense that, rather than being impregnated in a wash coat onto a monolithic carrier similar to automotive catalysts and diesel soot trap devices, the catalysts of the invention preferably are formed into particles, sometimes also referred to as beads or pellets, having any of a variety of shapes and the catalytic metals are provided to the reaction zone by placing a large number of these shaped catalysts in the reactor. Commonly encountered shapes include extrudates of arbitrary cross-section taking the form of a generalized cylinder in the sense that the generators defining the surface of the extrudate are parallel lines. As indicated above, any convenient particle shape including pellets, extrudates, spheres, spray dried microspheres, rings, pentarings, trilobes, quadrilobes and multi-lobal shapes may be used, although cylindrical pellets are preferred. Typically, the shapes are chosen empirically based upon perceived ability to contact the vapor phase with the catalytic agents effectively.

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment, when the catalyst support comprises high purity silica, with calcium metasilicate as a support modifier, the catalyst activity may extend or stabilize, the productivity and selectivity of the catalyst for prolonged periods extending into over one week, over two weeks, and even months, of commercially viable operation in the presence of acetic acid vapor at temperatures of 125° C. to 350° C. at space velocities of greater than 2500 $hr^{-1}$.

The catalyst compositions of the invention preferably are formed through metal impregnation of the modified support, although other processes such as chemical vapor deposition may also be employed. Before the metals are impregnated, it typically is desired to form the modified support, for example, through a step of impregnating the support material with the support modifier. A precursor to the support modifier, such as an acetate or a nitrate, may be used. Preferably, the precursor is soluble. In one aspect, the support modifier, e.g., $WO_3$ and/or $CaSiO_3$, is added to the support material, e.g., $SiO_2$. For example, an aqueous suspension of the support modifier may be formed by adding the solid support modifier to deionized water, followed by the addition of colloidal support material thereto. The resulting mixture may be stirred and added to additional support material using, for example, incipient wetness techniques in which the support modifier is added to a support material having the same pore volume as the volume of the support modifier solution. Capillary action then draws the support modifier into the pores in the support material. The modified support can then be formed by drying and calcining to drive off water and any volatile components within the support modifier solution and depositing the support modifiers on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours. Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support materials into desired size distribution can be employed. Calcining of the shaped modified support may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

In a preferred method of preparing the catalyst, the metals are impregnated onto the modified support. A precursor of the first metal (first metal precursor) preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. The second metal also preferably is impregnated into the modified support from a second metal precursor. If desired, a third metal or third metal precursor may also be impregnated into the modified support.

Impregnation occurs by adding, optionally drop wise, either or both the first metal precursor and/or the second metal precursor and/or additional metal precursors, preferably in suspension or solution, to the dry modified support. The resulting mixture may then be heated, e.g., optionally under vacuum, in order to remove the solvent. Additional drying, calcining may be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the first and second metals (and optional additional metals) into the modified support may occur simultaneously (co-impregnation) or sequentially. In simultaneous impregnation, the first and second metal precursors (and optionally additional metal precursors) are mixed together and added to the modified support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first and second metal precursors in the event the two precursors are incompatible with the desired solvent, e.g., water.

In sequential impregnation, the first metal precursor is first added to the modified support followed by drying and calcining, and the resulting material is then impregnated with the second metal precursor followed by an additional drying and calcining step to form the final catalyst composition. Additional metal precursors (e.g., a third metal precursor) may be added either with the first and/or second metal precursor or a separate third impregnation step, followed by drying and calcination. Of course, combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. Generally, both from the point of view of economics and environmental aspects, aqueous solutions of soluble compounds of platinum are preferred. In one embodiment, the first metal precursor is not a metal halide and is substantially free of metal halides. Without being bound to theory, such non-(metal halide) precursors are believed to increase selectivity to ethanol. A particularly preferred precursor to platinum is platinum ammonium nitrate, $Pt(NH_3)_4(NO_4)_2$.

In one aspect, the "promoter" metal or metal precursor is first added to the modified support, followed by the "main" or "primary" metal or metal precursor. Of course the reverse order of addition is also possible. Exemplary precursors for promoter metals include metal halides, amine solubilized metal hydroxides, metal nitrates or metal oxalates. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of the one or more metals, for example Pt and Sn.

As an example, $PtSn/WO_3/CaSiO_3$ on $SiO_2$ may be prepared by a first impregnation of $WO_3$ and $CaSiO_3$ onto the $SiO_2$, followed by the co-impregnation with $Pt(NH_3)_4(NO_4)_2$ and $Sn(AcO)_2$. Again, each impregnation step may be followed by drying and calcination steps. In most cases, the impregnation may be carried out using metal nitrate solutions. However, various other soluble salts, which upon calcination release metal ions, can also be used. Examples of other suitable metal salts for impregnation include, metal acids, such as perrhenic acid solution, metal oxalates, and the like. In those cases where substantially pure ethanol is to be produced, it is generally preferable to avoid the use of halogenated precursors for the platinum group metals, using the nitrogenous amine and/or nitrate based precursors instead.

The raw materials, acetic acid and hydrogen, fed to the primary reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Esters, such as ethyl acetate, n-propyl acetate, iso-propyl acetate, n-butyl acetate, and others, may also be present in the feed. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1. Generally, the reactor may use an excess of hydrogen, while the secondary hydrogenation reactor may use a sufficient amount of hydrogen as necessary to hydrogenate the impurities. In one aspect, a portion of the excess hydrogen from the reactor is directed to the secondary reactor for hydrogenation. In some optional embodiments, the secondary reactor could be operated at a higher pressure than the hydrogenation reactor and a high pressure gas stream comprising hydrogen may be separated from the secondary reactor liquid product in an adiabatic pressure reduction vessel, and the gas stream could be directed to the hydrogenation reactor system.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

In particular, the hydrogenation of acetic acid may achieve favorable conversion of acetic acid and favorable selectivity and productivity to ethanol in the primary reactor. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 70%, e.g., at least 75% or at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the reactor, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 5 to 70 | 5 to 50 |
| Water | 5 to 30 | 5 to 28 | 10 to 26 | 10 to 22 |

TABLE 1-continued

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 97 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The invention is described in detail below with reference to numerous embodiments for purposes of exemplification and illustration only. Modifications to particular embodiments within the spirit and scope of the present invention, set forth in the appended claims, will be readily apparent to those of skill in the art.

In order that the invention disclosed herein may be more efficiently understood, an example is provided below. It should be understood that these examples are for illustrative purposes only and is not to be construed as limiting the invention in any manner.

EXAMPLES

Example 1

Catalyst Preparation

A modified catalyst was prepared by adding $WO_3$ and $CaSiO_3$ to a $SiO_2$ catalyst support followed by the addition of a binary metal combination of Pt/Sn.

An aqueous suspension of $CaSiO_3$ ($\leqq 200$ mesh) was prepared and stirred for 2 hours at room temperature with $SiO_2$. In addition, a solution of a soluble $WO_3$ precursor $(NH_4)_6H_{12}W_{12}O_{40} \cdot nH_2O$ (AMT) was added drop wise to the $SiO_2$ in a flask. The amount of the $CaSiO_3$ and $WO_3$ varied for each of the catalyst depending on the molar ratio. The catalyst was dried overnight at 120° C. followed by calcination at 500° C. for 6 hours. After the modified support was made, precursors to the binary metals were added and calcined. The metal loading of the binary mixture was less than 5 wt.%, based on the total weight of the catalyst, was the same for each catalyst.

The following three catalysts were made according to this example:
A) $SiO_2$—$CaSiO_3$ (6 wt. %)-Pt—Sn
B) $SiO_2$—$CaSiO_3$ (6 wt. %)-$WO_3$ (8 wt. %)-Pt—Sn
C) $SiO_2$—$CaSiO_3$ (6 wt. %)-$WO_3$ (12 wt. %)-Pt—Sn The molar ratio of Ca to W in Catalyst B is 1.3:1, and in Catalyst C is 1:1. Catalyst A contains only the $CaSiO_3$ support modifier and does not contain any $WO_3$.

Example 2

Hydrogenation

Vaporized acetic acid and hydrogen were passed over each of the catalysts prepared in Example 1. The reaction conditions were the same for each reaction. The results are indicated in Table 2.

TABLE 2

| Catalyst | Ca/W Ratio | HOAc Conv. (%) | Selectivity (%) EtOH | Selectivity (%) EtOAc | EtOH Yield (%) | Productivity (g/kg/hr) |
|---|---|---|---|---|---|---|
| A | — | 71 | 81 | 15 | 57 | 619 |
| B | 1.3:1 | 94 | 75 | 24 | 71 | 721 |
| C | 1:1 | 98 | 70 | 29 | 69 | 703 |

Catalysts B and C demonstrate an improvement of productivity and acetic acid conversion over Catalyst A. As the $WO_3$ amount increases beyond 12 wt. %, the acetic acid conversion and ethanol selectivity generally remains similar to Catalyst C.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing alcohol comprising:
 passing a gaseous stream comprising hydrogen and an alkanoic acid in the vapor phase over a hydrogenation catalyst to yield an alcohol, wherein the hydrogenation catalyst comprising a support and one or more metals, wherein the hydrogenation catalyst further comprises:
 (a) tungsten oxide, and
 (b) at least one alkaline earth metal oxide, at least one alkaline earth metal metasilicate, or mixtures thereof.

2. The process of claim 1, wherein the molar ratio, based on the metals, of component (b) to component (a) is from 1:3 to 5:1.

3. The process of claim 1, wherein the support is selected from the group consisting of silica, silica/alumina, calcium metasilicate, pyrogenic silica, high purity silica, and mixtures thereof 4. The process of claim 1, wherein the support is present in an amount from 25 wt. % to 99 wt. %.

5. The process of claim 1, wherein the one or more metals are selected from the group consisting of tin, rhodium, platinum, palladium, cobalt, copper, iron, nickel, zinc, chromium, rhenium, molybdenum, and ruthenium.

6. The process of claim 1, wherein the total weight of the one or more metals is from 0.1 to 25 wt. %.

7. The process of claim 1, wherein the tungsten oxide is present in an amount from 1 to 25 wt. %.

8. The process of claim 1, wherein the alkaline earth metal of the at least one oxide or metasilicate is selected from the group consisting of magnesium, calcium, and mixtures thereof 9. The process of claim 1, wherein the alkaline earth metal metasilicate is a calcium metasilicate.

10. The process of claim 1, wherein the alkanoic acid is formed from methanol and carbon monoxide, wherein at least one of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof 11. The process of claim 1, wherein the gaseous stream is passed over the hydrogenation catalyst at a temperature from 125° C. to 350° C.

12. The process of claim 1, wherein the molar ratio of hydrogen to alkanoic acid is greater than 2:1.

13. A process for producing alcohol comprising:
 passing a gaseous stream comprising hydrogen and an alkanoic acid in the vapor phase over a hydrogenation catalyst to yield an alcohol, wherein the hydrogenation catalyst comprises:
 (a) support,
 (b) tin,
 (c) one or more metals selected from the group consisting of rhodium, platinum, palladium, cobalt, copper, iron, nickel, zinc, chromium, rhenium, molybdenum, and ruthenium,
 (d) tungsten oxide, and
 (e) at least one alkaline earth metal oxide and alkaline earth metal metasiliciate.

14. The process of claim 13, wherein the molar ratio, based on the metals, of component (b) to component (a) is from 1:3 to 5:1.

15. A hydrogenation catalyst for producing alcohol, the hydrogenation catalyst comprises a support and one or more metals, wherein the hydrogenation catalyst further comprises:
 (a) tungsten oxide,
 (b) at least one alkaline earth metal oxide, at least one alkaline earth metal metasilicate, or mixtures thereof, and
 wherein the molar ratio, based on the metals, of component (b) to component (a) is from 1:3 to 5:1.

16. The catalyst of claim 15, wherein the support is selected from the group consisting of silica, silica/alumina, calcium metasilicate, pyrogenic silica, high purity silica, and mixtures thereof 17. The catalyst of claim 15, wherein the support is present in an amount from 25 wt. % to 99 wt. %.

18. The catalyst of claim 15, wherein the one or more metals are selected from the group consisting of tin, rhodium, platinum, palladium, cobalt, copper, iron, nickel, zinc, chromium, rhenium, molybdenum, and ruthenium.

19. The catalyst of claim 15, wherein the total weight of the one or more metals is from 0.1 to 25 wt. %.

20. The catalyst of claim 15, wherein the alkaline earth metal of the at least one oxide or metasilicate is selected from the group consisting of magnesium, calcium, and mixtures thereof.

21. The catalyst of claim 15, wherein the alkaline earth metal metasilicate is a calcium metasilicate.

22. A hydrogenation catalyst for producing alcohol, the hydrogenation catalyst comprising:
 (a) support,
 (b) tin,
 (c) one or more metals selected from the group consisting of rhodium, platinum, palladium, cobalt, copper, iron, nickel, zinc, chromium, rhenium, molybdenum, and ruthenium,
 (d) tungsten oxide,
 (e) at least one alkaline earth metal oxide and alkaline earth metal metasilicate, and wherein the molar ratio, based on the metals, of component (e) to component (d) is from 1:3 to 5:1.

* * * * *